(12) United States Patent
Taylor

(10) Patent No.: US 9,335,248 B1
(45) Date of Patent: May 10, 2016

(54) SYSTEMS AND METHODS FOR QUANTIFYING PARTICLE PERFORMANCE IN A SUBSTRATE PROCESSING SYSTEM

(71) Applicant: Lam Research Corporation, Fremont, CA (US)

(72) Inventor: Travis R. Taylor, Fremont, CA (US)

(73) Assignee: LAM RESEARCH CORPORATION, Fremont, CA (US)

(*) Notice: Subject to any disclaimer, the term of this patent is extended or adjusted under 35 U.S.C. 154(b) by 0 days.

(21) Appl. No.: 14/639,275

(22) Filed: Mar. 5, 2015

(51) Int. Cl.
*G01N 15/14* (2006.01)

(52) U.S. Cl.
CPC ........ *G01N 15/1434* (2013.01); *G01N 15/1404* (2013.01); *G01N 2015/1486* (2013.01)

(58) Field of Classification Search
CPC .......... G01N 15/1404; G01N 15/1434; G01N 2015/1486
See application file for complete search history.

(56) References Cited

PUBLICATIONS

"Process for Preparing Macroscopic Quantities of Brightly Photoluminescent Silicon Nanoparticles with Emission, Spanning the Visible Spectrum", Xuegeng Li, Yuanqing He, Suddha S. Talukdar, and Mark T. Swihart★, Jul. 10, 2003, Langmuir 2003, 19, p. 8490-8496.

*Primary Examiner* — Mark R Gaworecki

(57) ABSTRACT

A method for diagnosing a particle removal system of a substrate processing system includes dispersing synthetic particles onto a substrate; exciting the synthetic particles using a light source having a first predetermined wavelength; measuring photoluminescence of the synthetic particles at a second predetermined wavelength that is different than the first predetermined wavelength and determining a first number of the synthetic particles on the substrate; at least one of moving the substrate through a chamber or processing the substrate in the chamber of the substrate processing system; exciting the synthetic particles using light having the first predetermined wavelength; measuring photoluminescence of the synthetic particles at the second predetermined wavelength that is different than the first predetermined wavelength; and determining a second number of the synthetic particles on the substrate based on the measuring.

29 Claims, 5 Drawing Sheets

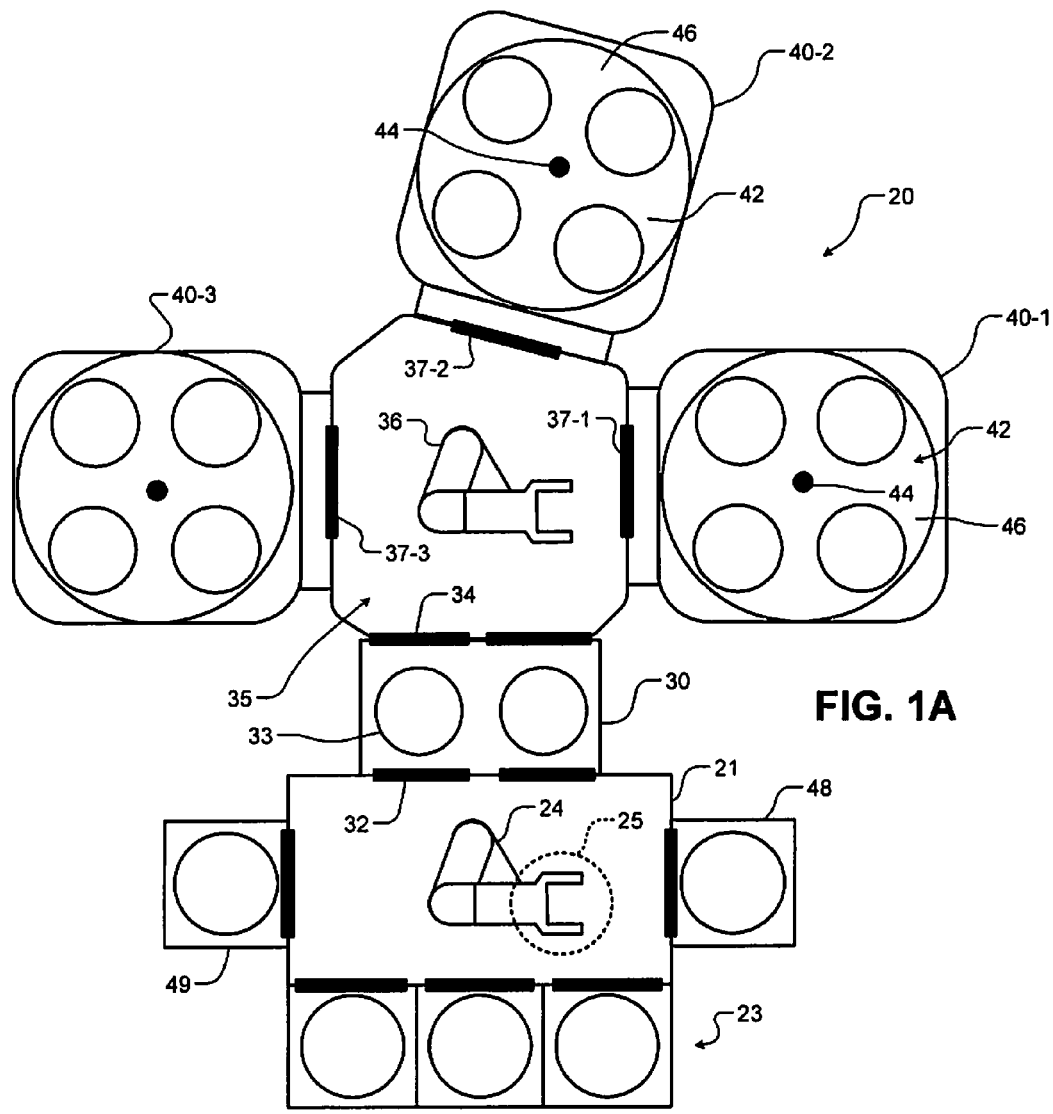
FIG. 1A
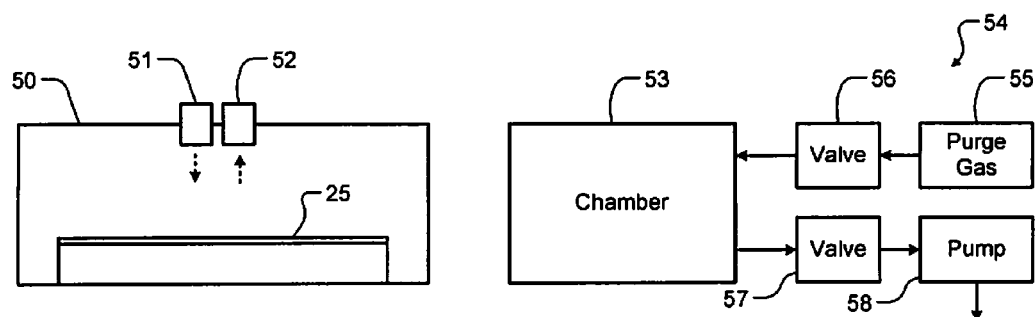
FIG. 1B     FIG. 1C

SYSTEMS AND METHODS FOR QUANTIFYING PARTICLE PERFORMANCE IN A SUBSTRATE PROCESSING SYSTEM

FIELD

The present disclosure relates to substrate processing systems, and more particularly to systems and methods for quantifying particle performance in a substrate processing system.

BACKGROUND

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Substrate processing systems may be used to perform deposition and/or etching of film on a substrate such as a semiconductor wafer. Substrate processing systems typically include one or more processing chambers each with a substrate support such as a pedestal, an electrostatic chuck, a plate, etc. A transport handling chamber including one or more robots may be used to receive the substrates and to move the substrates to the one or more processing chambers for processing. After processing, the one or more robots move the substrates from the processing chamber back to the cassette.

For example only, in a chemical vapor deposition (CVD) process, a gas mixture including one or more precursors may be introduced into the processing chamber to deposit a film on the substrate or to etch the substrate. In some processes, radio frequency (RF) plasma may be used to activate chemical reactions. Some chemical reactions that happen in the gas phase generate particles that may remain in the processing chamber after processing is completed. In addition to the particles created during processing, particles may also reach the processing chamber or transport handling chamber due to dusted upstream parts, chamber leak events, contamination that occurs when replacing parts, and/or contamination that occurs during maintenance.

Some processes require substrates to meet or exceed a particle count standard or the substrates need to be rejected. For example only, one industry standard for particles on a substrate is <50 particles that have a size >45 nm. As the minimum feature sizes continue to shrink, the industry standards for particles will be specified for smaller particle sizes.

Currently, light scattering may be used to detect on-wafer particles. Synthetic particles of a known size, shape, and composition are systematically placed on a substrate. The substrate is rotated and bombarded with a single wavelength of light. The reflected light is measured and stored. The process is repeated for a range of synthetic particles sizes of a known shape and composition. This process establishes a correlation between the particle size and intensity of scattered light.

Later, substrates with particles of unknown size, shape, and composition are rotated and the scattered light is compared to the known scattering intensities. Interpolation and extrapolation may be used to correlate the scattering light intensity with particle size. The particle sizes that can be measured are constrained by the wavelength of the light source for scattering. The size of the particles that are detected is a function of the wavelength. Smaller wavelengths of light can detect smaller particles. As the wavelengths of light decrease below the vacuum ultraviolet limit (<200 nm), several issues arise that make the light scattering method more difficult. For example below 200 nm, air begins to ionize. This decreases the intensity of the light and invokes interactions that decrease the signal to noise ratio. The light scattering method has been used to detect particles down to 26 nm.

SUMMARY

A method for diagnosing a particle removal system of a substrate processing system includes dispersing synthetic particles onto a substrate; exciting the synthetic particles using a light source having a first predetermined wavelength; measuring photoluminescence of the synthetic particles at a second predetermined wavelength that is different than the first predetermined wavelength and determining a first number of the synthetic particles on the substrate; at least one of moving the substrate through a chamber or processing the substrate in the chamber of the substrate processing system; exciting the synthetic particles using light having the first predetermined wavelength; measuring photoluminescence of the synthetic particles at the second predetermined wavelength that is different than the first predetermined wavelength; and determining a second number of the synthetic particles on the substrate based on the measuring.

In other features, the synthetic particles have N different sizes, wherein N is an integer greater than one. The light source produces light at N first predetermined wavelengths and measurement is made at N second predetermined wavelengths. N first predetermined wavelengths are distinct. The N second predetermined wavelengths are distinct. Excitation at the N first predetermined wavelengths and measurement at the N second predetermined wavelengths are performed sequentially, respectively. Excitation at the N first predetermined wavelengths and measurement at the N second predetermined wavelengths are performed in an overlapping manner or a partially overlapping manner, respectively.

In other features, the chamber is selected from a group consisting of a transport handling chamber, a buffer station, a metrology station and a processing chamber of the substrate processing system. The synthetic particles have a size between 5 nm and 30 nm.

In other features, the method includes diagnosing operation of a particle removal system associated with the chamber based on the first count and the second count. The method includes altering operation of a particle removal system associated with the chamber based on the first count and the second count.

A method for diagnosing particle movement in a chamber of a substrate processing system includes dispersing synthetic particles into the chamber of the substrate processing system; at least one of operating the chamber or moving the substrate through the chamber of the substrate processing system; exciting the synthetic particles using light having a first predetermined wavelength; measuring photoluminescence of the synthetic particles at a second predetermined wavelength that is different than the first predetermined wavelength; and determining a number of the synthetic particles that moved from the chamber onto the substrate based on the measuring.

In other features, prior to the at least one of operating the chamber or moving the substrate through the chamber, exciting the synthetic particles using light having a first predetermined wavelength; measuring photoluminescence of the synthetic particles at a second predetermined wavelength that is different than the first predetermined wavelength; and determining a first number of the synthetic particles on the substrate.

In other features, the synthetic particles have N different sizes, wherein N is an integer greater than one. The light source produces light at N first predetermined wavelengths and measurement is made at N second predetermined wavelengths. The N first predetermined wavelengths are distinct, and the N second predetermined wavelengths are distinct. Excitation at the N first predetermined wavelengths and measurement at the N second predetermined wavelengths are performed sequentially, respectively. Excitation at the N first predetermined wavelengths and measurement at the N second predetermined wavelengths are performed in an overlapping manner or a partially overlapping manner, respectively.

In other features, the chamber is selected from a group consisting of a transport handling chamber, a buffer station, a metrology station and a processing chamber of the substrate processing system. The synthetic particles have a size between 5 nm and 30 nm. The method includes diagnosing operation of a particle removal system associated with the chamber based on the first count and the second count. The method includes altering operation of a particle removal system associated with the chamber based on the first count and the second count.

A method for determining particle adders in a substrate processing system includes at least one of operating a chamber or moving the substrate through the chamber of the substrate processing system; exciting particles on the substrate using light having N first predetermined wavelengths, where N is an integer greater than one; measuring photoluminescence of the particles at N second predetermined wavelengths that are different than the N first predetermined wavelengths; and determining a number of the particles on the substrate based on the measuring.

In other features, prior to moving the substrate through the chamber, exciting particles on the substrate using light having the N first predetermined wavelengths; and measuring photoluminescence of the synthetic particles at N second predetermined wavelengths that are different than the N first predetermined wavelengths and determining an initial number of the particles on the substrate.

In other features, the particles have at least N different sizes. The N first predetermined wavelengths are distinct, and the N second predetermined wavelengths are distinct. The excitation at the N first predetermined wavelengths and measurement at the N second predetermined wavelengths is performed sequentially, respectively. The excitation at the N first predetermined wavelengths and measurement at the N second predetermined wavelengths is performed in an overlapping manner or a partially overlapping manner, respectively. The chamber is selected from a group consisting of a transport handling chamber, a buffer station, a metrology station and a processing chamber of the substrate processing system. The particles have a size between 5 nm and 30 nm.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein:

FIG. 1A is a functional block diagram of an example of a substrate processing system according to the present disclosure;

FIG. 1B is a functional block diagram of an example of a photoluminescence measuring system according to the present disclosure;

FIG. 1C is a functional block diagram of an example of a purge/vent system according to the present disclosure;

In the drawings, reference numbers may be reused to identify similar and/or identical elements.

DETAILED DESCRIPTION

Figure 2A:
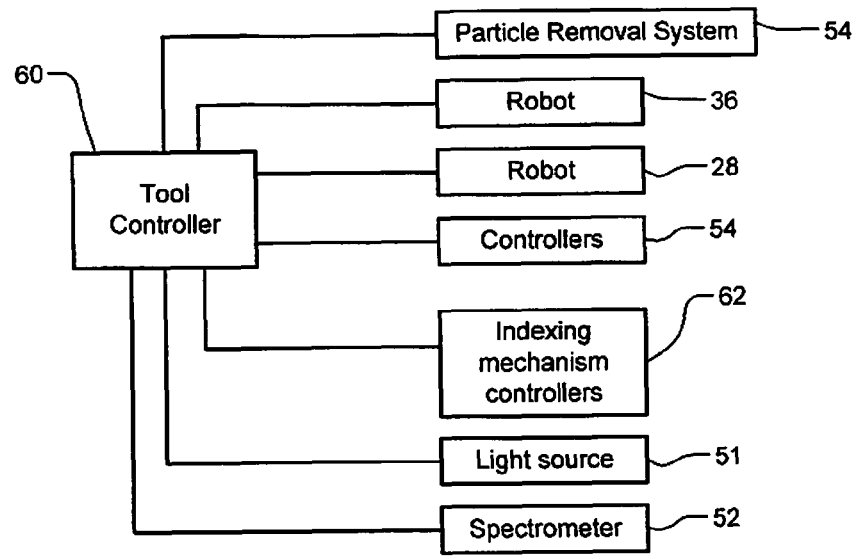
FIGS. 2A and 2B are functional block diagrams of an example of a tool controller for a substrate processing system according to the present disclosure.

As the particle size decreases and the particle surface area to volume ratio increases, quantum mechanical properties of the particle change. As a result, the particle has different physical and spectroscopic properties as compared to the bulk material of the same composition. These effects can be observed for example with particle sizes less than 100 nm diameter. The new quantum mechanical properties impact how the particle absorbs and emits light.

Systems and methods described herein measure photoluminescence of natural and/or synthetic particles. Photoluminescence occurs when matter absorbs light at one wavelength and emits light at another wavelength. According to the present disclosure, synthetic nanoparticles as small as 5 nm can be detected as a single particle using the photoluminescent effect. For example only, the synthetic particles may be made in a manner described in "Process for Preparing Macroscopic Quantities of Brightly Photoluminescent Silicon Nanoparticles with Emission, Spanning the Visible Spectrum", Xuegeng Li, Yuanqing He, Suddha S. Talukdar, and Mark T. Swihart*, Langmuir 2003, 19, 8490-8496, or using any other suitable processes.

As will be described below, natural particles may also have photoluminescent properties and can also be detected with the same methodology as synthetic nanoparticles. Systems and methods described herein use the photoluminescent properties of natural and synthetic nanoparticles to quantify particle performance for substrate processing systems.

Systems and methods described herein employ one or more light sources to provide light at N first wavelengths. The light is absorbed by the particles and a spectrometer detects the re-emitted light at N second wavelengths that are different than the N first wavelengths, where N is an integer greater than zero. In some examples, N=1. In other examples, N>1.

When a photon is absorbed by particles, the particles can emit photons that have higher or lower wavelengths than the incident photons. It is more common to have higher wavelengths. Higher wavelengths correspond to lower energy photons. When the emitted photon has lower energy, some of the energy was lost to the particles.

Conversely energy that is already stored in the particles can also be coupled with the energy of the incident photons and result in emitted photons that have higher energy than the incident photons (which corresponds to a lower wavelength).

In addition, a range of particle sizes can absorb light at a single wavelength but emit at light at several different wavelengths.

The systems and methods described herein can be used to detect both natural and synthetic nanoparticles. Synthetic nanoparticles can be engineered to have specific photoluminescent properties. The knowledge of the absorbing and photoluminescent wavelengths of synthetic particles makes it easier to design equipment to detect the synthetic particles. In the case of natural particles where the absorbing and photoluminescent wavelengths are unknown, multiple light sources at different wavelengths and spectrometers monitoring multiple wavelengths may be used.

For example only, synthetic nanoparticles may be dispersed onto a substrate such as a semiconductor wafer. The number of particles that are dispersed may be pre-measured. The substrate may be moved through a chamber (e.g., handled by transfer handling chamber, stored in a buffer station, analyzed in a metrology station, processed in a processing chamber) of a substrate processing system. Then, the number of particles may be measured on the substrate. The difference in the two measurements may be used to determine size dependent information about the efficiency of particle removal systems associated with the chamber. In other words, this technique can be used to diagnose operation of the particle removal systems in the chamber. For example, the information can be used to increase the efficiency of removing particles of predetermined sizes from the substrates.

While FIGS. 1A-1C set forth below show various arrangements of substrate processing systems, the systems and methods described herein have application to other arrangements of substrate processing systems and/or to other portions of the substrate processing systems.

An example of a substrate processing system is presented herein for illustration purposes only. Other substrate processing system arrangements may be used. In FIG. 1A, a substrate processing tool 20 includes a transport handling chamber 21 and multiple reactors each with one or more substrate processing chambers. A substrate 25 enters the substrate processing tool 20 from a cassette and/or pod 23, such as a front opening unified pod (FOUP). A robot 24 includes one or more end effectors to handle the substrate 25. A pressure of the transport handling chamber 21 may be at atmospheric pressure. Alternately, the transport handling chamber 21 may be at vacuum pressure (with ports acting as isolation valves).

The robot 24 moves the substrates 25 from the cassette and/or pod to a load lock 30. For example, the substrate 25 enters the load lock 30 through a port 32 (or isolation valve) and is placed on a load lock pedestal 33. The port 32 to the transport handling chamber 21 closes and the load lock 30 is pumped down to an appropriate pressure for transfer. Then a port 34 opens and another robot 36 (also with one or more end effectors) in a processing handling chamber 35 places the substrates through one of the ports 37-1, 37-2, 37-3 (collectively ports 37) corresponding to a selected reactor 40-1, 40-2, and 40-3 (collectively reactors 40).

A substrate indexing mechanism 42 may be used to further position the substrates relative to the substrate processing chambers. In some examples, the indexing mechanism 42 includes a spindle 44 and a transfer plate 46.

In some examples, at least one of the processing chambers or stations of the reactors 40 is capable of performing semiconductor processing operations, such as a material deposition or etch, sequentially or simultaneously with the other stations. In some examples, at least one or more of the stations may perform RF-based semiconductor processing operations.

The substrate is moved from one station to the next in the reactor 40 using the substrate indexing mechanism 42. One or more of the stations of the reactors 40 may be capable of performing RF plasma deposition or etching. During use, the substrates are moved to one or more of the reactors 40, processed and then returned.

The substrate processing tool 20 may include one or more metrology stations 48 (such as a mass metrology station). In FIG. 1A, while the metrology station 48 is connected to the transport handling chamber 21, the metrology station 48 may be connected to the processing handling chamber 35. In some examples, the substrate processing tool 20 includes one or more buffer stations 49.

In one example, a substrate is received, moved to one of the reactors 40-1 for processing, moved to the metrology station 48, moved to another one of the reactors 40-2 for processing, moved to the metrology station 48, moved to another one of the reactors 40-3 for processing and then returned to the cassette.

Referring now to FIG. 1B, N light sources 51 generate light at N first predetermined wavelengths onto a surface of the substrate 25 in a chamber 50, where $N \geq 1$. The N first predetermined wavelengths may be selected based upon sizes/volumes of natural or synthetic particles that are expected to be present in the chamber 50. For example only, the chamber 50 may correspond to the transport handling chamber 21, the load lock 30, the metrology station 48, the buffer station 49, or another chamber in the substrate processing system 20. As can be appreciated, the chamber 50 may correspond to the chamber that is being diagnosed or a chamber that is connected to the chamber that is being diagnosed. In other words, particle performance of the transport handling chamber 21 may be at issue and the initial and subsequent measurements may be made in the transport handling chamber 21 or in chambers connected to the transport handling chamber 21 (such as the metrology station 48, the buffer station 49, the load lock 30, etc.).

One or more spectrometers 52 measure light emitted by the particles on the substrate 25 at N second predetermined wavelengths. The N second predetermined wavelengths may be selected based upon the expected spectroscopic properties based on the size, shape, and composition of the natural or synthetic particles that may be present in the chamber.

Referring now to FIG. 1C, a particle reduction system 54 reduces particles in a chamber 53. In some examples, the particle reduction system may include a purge/vent system. The chamber 53 may correspond to any one of the chambers of the substrate processing system.

For example, the particle reduction system 54 may include a purge gas source 55 and a valve 56 to selectively supply a purge gas to the chamber 53. A valve 57, a pump 58 and an exhaust system 59 may be used to vent or remove the particles from the chamber. The particle reduction system 54 may cycle purge gas for a predetermined period to remove particles from the chamber 53.

Figure 2B:
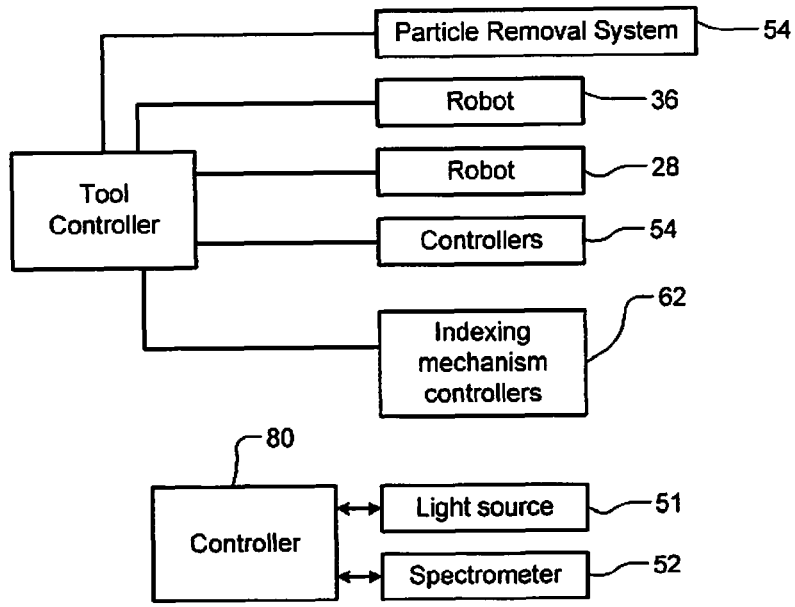

Referring now to FIGS. 2A and 2B, a tool controller 60 may be used to operate the substrate processing system. The tool controller 60 may communicate with one or more station controllers 54 that are associated with each of the stations of the reactors 40. Alternately, the substrate processing tool controller 60 and the station controllers 54 may be combined. The tool controller 60 also communicates with substrate handling robots such as robots 24 and 36 and indexing mechanism controllers 62 to coordinate movement of the substrates and indexing of the substrates in each of the reactors 40. The tool controller 60 may also communicate with the light source 51 and the spectrometer 52. However, the light source 51 and spectrometer 52 may be arranged as a separate system that is not connected to the tool controller or other components of the substrate processing system as shown in FIG. 2B. In some examples, a controller 80 communicates with and controls the light source 51 and the spectrometer 52.

Figure 3:
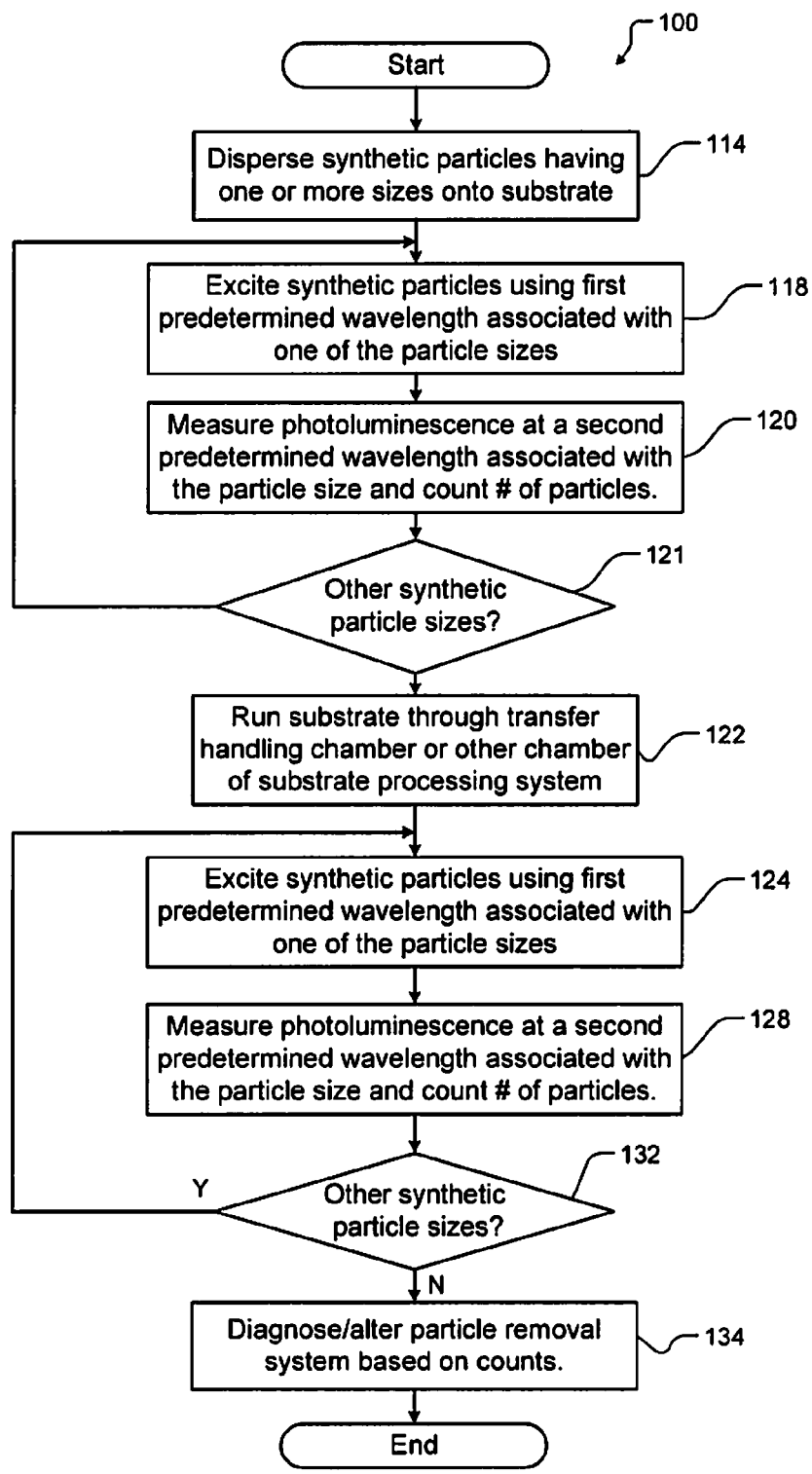
FIG. 3 is a flowchart illustrating an example of a method for diagnosing particle performance using synthetic particles according to the present disclosure.

Referring now to FIG. 3, a method 100 for diagnosing particle performance of a particle removal system for a chamber of a substrate processing system is shown. At 114, one or more different sizes of synthetic particles are dispersed onto a substrate. At 118, the synthetic particles are excited using light at a predetermined first wavelength corresponding to one of the particle sizes. At 120, the photoluminescence of the particles is measured at a predetermined second wavelength (that corresponds to one of the particle sizes and that is different than the first predetermined wavelength). The number of particles is determined. At 121, the process may be repeated for other particle sizes if needed. While the process may proceed sequentially for each particle size, the process may also be performed in an overlapping or partially overlapping manner. In other words, multiple different wavelengths may be used to excite the different particle sizes at the same time and photoluminescence at multiple different wavelengths may be measured at the same time.

At 122, the substrate is moved through a transfer handling chamber or other chamber of the substrate processing system. The chamber may be not operated or operated in a typical manner that would otherwise occur during normal operation of the chamber. Then, the substrate may be evaluated in the same chamber or moved to another chamber and evaluated. At 124, the synthetic particles are excited using light at the predetermined first wavelength associated with one of the particle sizes. At 128, the photoluminescence of the particles is measured at the predetermined second wavelength associated with the particle size and the number of particles is determined. At 132, the process may optionally be repeated for other synthetic particle sizes (and control may return to 124). As stated above, the process may be sequential or fully or partially overlapping. After the measurements are complete, operation of the particle removal system is diagnosed and/or altered based on the results at 134. The method 100 may be repeated one or more times.

Figure 4:
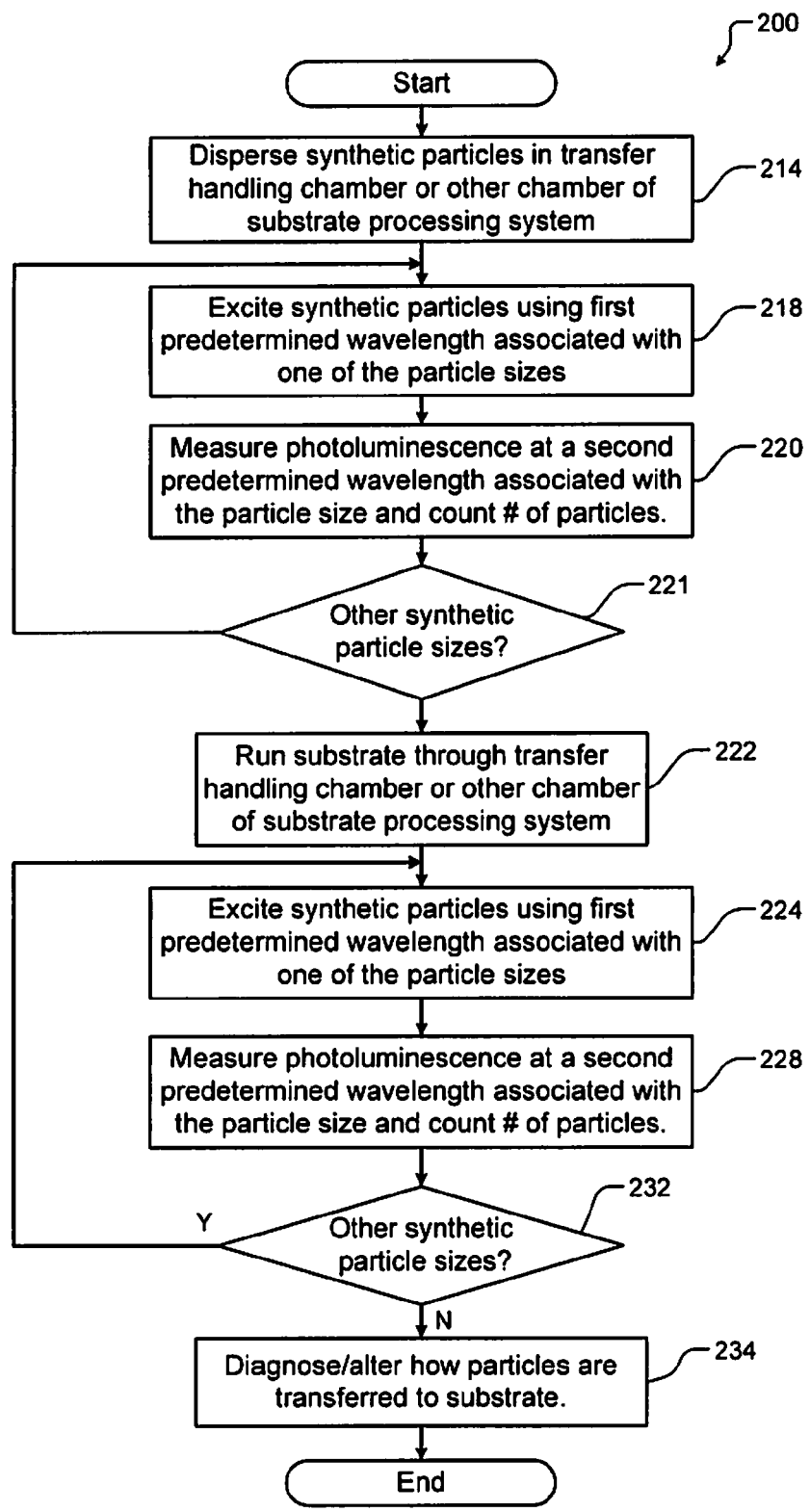
FIG. 4 is a flowchart illustrating another example of a method for diagnosing particle performance using synthetic particles according to the present disclosure.

For example only, the design or operating parameters of the particle removal system may be altered based on the results of the method in FIG. 4. For example only, the location of vent and purge openings may be optimized. In other examples, the vacuum pressures, flow rates, number of cycles or other process parameters may be evaluated, adjusted and/or optimized based on the results of the method in FIG. 4.

Referring now to FIG. 4, a method 200 for diagnosing particle movement from a chamber onto a substrate during substrate handling or processing is shown. At 214, one or more different sizes of synthetic particles are dispersed at predetermined locations in a transfer handling chamber or other chamber of a substrate processing system. If there is a chance that natural particles may be excited by wavelengths to be used during measurement, the number of particles can optionally be pre-measured before proceeding.

If pre-measurement is not to be performed, steps 218-221 can be skipped. Otherwise at 218, the substrate is optionally excited using light at a predetermined first wavelength corresponding to one of the particle sizes. At 220, the photoluminescence of the particles is optionally measured at a predetermined second wavelength (that corresponds to the particle size and that is different than the first predetermined wavelength) and the number of particles is determined. At 221, the process may be repeated for other particle sizes if needed. While the process may proceed sequentially for each particle size, the process may be performed in an overlapping or partially overlapping manner. In other words, multiple different wavelengths may be used to excite the different particle sizes at the same time and multiple different wavelengths may be measured at the same time.

At 222, the substrate is moved through the transfer handling chamber or other chamber of the substrate processing system where the synthetic particles were distributed. As can be appreciated, the chamber may be not operated or operated in a manner that is typical for normal operation of the chamber. During operation, some of the synthetic particles may be transferred to the substrate. The substrate may be evaluated in the same chamber or be moved to another chamber for evaluation.

At 224, the substrate is excited using the predetermined first wavelength value or range associated with one of the particle sizes. At 228, the photoluminescence of the particles is measured at the predetermined second wavelength value associated with the particle size and the number of particles is determined. At 232, the process may optionally be repeated for other synthetic particle sizes (and control may return to 224). As stated above, the process may be sequential or fully or partially overlapping. As a result, particle movement in the chamber can be diagnosed in part based on the results at 234. The method 200 may be repeated one or more times.

Figure 5:
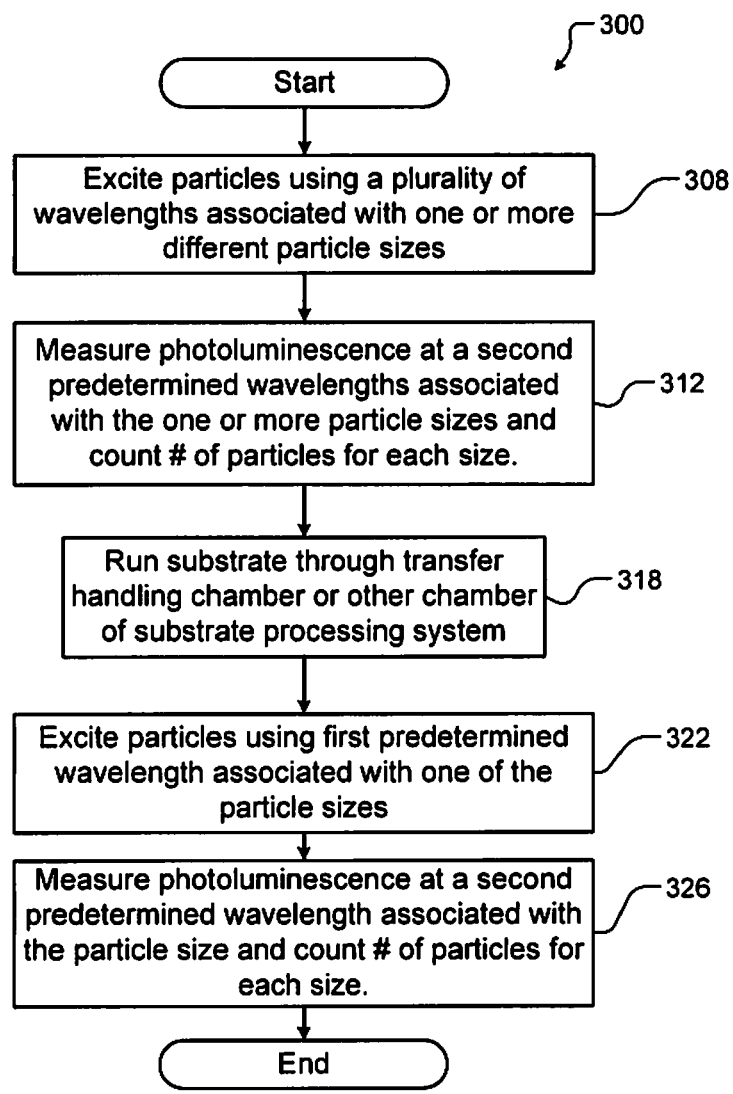
FIG. 5 is a flowchart illustrating another example of a method for diagnosing particle performance using natural particles according to the present disclosure.

Referring now to FIG. 5, a method 300 for determining the number of natural particles in a substrate processing chamber is shown. At 308, the natural particles are excited using light at a plurality of first wavelengths corresponding to one or more different particle sizes. At 312, the photoluminescence of the particles is measured at second predetermined wavelengths (that correspond to the particle sizes and that are different than the first predetermined wavelength values or ranges). The number of particles for each particle size is determined. The measurement can be performed sequentially or in an overlapping or partially overlapping manner. The process may end at this point or may continue after moving the substrate through a chamber.

At 322, the substrate may be moved through a transfer handling chamber or other chamber of the substrate processing system. The chamber may be not operated or operated in a manner that is typical for normal operation of the substrate processing system. At 324, the particles are excited using the predetermined first wavelengths associated with the particle sizes. At 228, the photoluminescence of the particles is measured at the predetermined second wavelengths associated with the particle sizes and the number of particles for each size is determined. As stated above, the process may be sequential or fully or partially overlapping.

As can be appreciated, the excitation and measurement wavelengths for the synthetic and natural particles may be determined in advance using known natural or synthetic particles. Then the known responses can be used with the unknown responses during measurement. Extrapolation or interpolation may be used in the process of identifying the sizes of the particles.

The systems and methods according to the present disclosure enable measurement of particles at small sizes and quantities at a time when the industry cannot make a wafer to the same cleanliness standard.

When using the synthetic particle embodiments, the systems and methods described herein are generally insensitive to the total number of particles on the substrate before the substrate enters the system because the natural particles will probably not emit light at the photoluminescent wavelengths. Light scattering techniques detect the total number of particles. However, the systems and methods described herein may be used to only detect the particles with specific photoluminescent characteristics, which correspond to specific particle sizes.

The light scattering technique has a detection efficiency that decreases as the particle size decreases. This means that the total number of particles added during a test is a function of the number of particles that were present during the pre-measurement. For example if there are 200 particles during pre-measurement and the measurement efficiency is 90% then there are 20 particles that were not measured during the pre-measurement. During the post-measurement, some of the 20 particles may be detected and will be reported as adders. In the extreme case where all of the 20 particles are detected during post-measurement, the analysis will show 20 particles were added to the substrate, which is not true. The particles were already there, but were not detected during the first light scattering measurement.

Industry standard for particles wafers is <50 adders for >45 nm. Particle reduction development for particles >30 nm is currently being done. Substrates from vendors can have 100-200 particles between 30 nm-45 nm. A typical particle target is 5 adders >30 nm. In the example set forth above, the potential adders due to the particle detection efficiency can be 20. When the specification is 5 adders, a situation involving measurement efficiency of 90% and a pre-measurement particle count of 200 is unsatisfactory. In practice, substrates with >100 particles that are >30 nm are discarded, which becomes expensive.

The systems and methods using synthetic nanoparticles are only sensitive to the photoluminescence of the natural and synthetic nanoparticles. All of the other particles are not detected. In some situations it will be safe to assume that the number of photoluminescent particles on the substrate during pre-measurement is zero. In these examples, the pre-measurement may be avoided, which saves on metrology time.

In some implementations, a controller is part of a system, which may be part of the above-described examples. Such systems can comprise semiconductor processing equipment, including a processing tool or tools, chamber or chambers, a platform or platforms for processing, and/or specific processing components (a wafer pedestal, a gas flow system, etc.). These systems may be integrated with electronics for controlling their operation before, during, and after processing of a semiconductor wafer or substrate. The electronics may be referred to as the "controller," which may control various components or subparts of the system or systems. The controller, depending on the processing requirements and/or the type of system, may be programmed to control any of the processes disclosed herein, including the delivery of processing gases, temperature settings (e.g., heating and/or cooling), pressure settings, vacuum settings, power settings, radio frequency (RF) generator settings, RF matching circuit settings, frequency settings, flow rate settings, fluid delivery settings, positional and operation settings, wafer transfers into and out of a tool and other transfer tools and/or load locks connected to or interfaced with a specific system.

Broadly speaking, the controller may be defined as electronics having various integrated circuits, logic, memory, and/or software that receive instructions, issue instructions, control operation, enable cleaning operations, enable endpoint measurements, and the like. The integrated circuits may include chips in the form of firmware that store program instructions, digital signal processors (DSPs), chips defined as application specific integrated circuits (ASICs), and/or one or more microprocessors, or microcontrollers that execute program instructions (e.g., software). Program instructions may be instructions communicated to the controller in the form of various individual settings (or program files), defining operational parameters for carrying out a particular process on or for a semiconductor wafer or to a system. The operational parameters may, in some embodiments, be part of a recipe defined by process engineers to accomplish one or more processing steps during the fabrication of one or more layers, materials, metals, oxides, silicon, silicon dioxide, surfaces, circuits, and/or dies of a wafer.

The controller, in some implementations, may be a part of or coupled to a computer that is integrated with the system, coupled to the system, otherwise networked to the system, or a combination thereof. For example, the controller may be in the "cloud" or all or a part of a fab host computer system, which can allow for remote access of the wafer processing. The computer may enable remote access to the system to monitor current progress of fabrication operations, examine a history of past fabrication operations, examine trends or performance metrics from a plurality of fabrication operations, to change parameters of current processing, to set processing steps to follow a current processing, or to start a new process. In some examples, a remote computer (e.g. a server) can provide process recipes to a system over a network, which may include a local network or the Internet. The remote computer may include a user interface that enables entry or programming of parameters and/or settings, which are then communicated to the system from the remote computer. In some examples, the controller receives instructions in the form of data, which specify parameters for each of the processing steps to be performed during one or more operations. It should be understood that the parameters may be specific to the type of process to be performed and the type of tool that the controller is configured to interface with or control. Thus as described above, the controller may be distributed, such as by comprising one or more discrete controllers that are networked together and working towards a common purpose, such as the processes and controls described herein. An example of a distributed controller for such purposes would be one or more integrated circuits on a chamber in communication with one or more integrated circuits located remotely (such as at the platform level or as part of a remote computer) that combine to control a process on the chamber.

Without limitation, example systems may include a plasma etch chamber or module, a deposition chamber or module, a spin-rinse chamber or module, a metal plating chamber or module, a clean chamber or module, a bevel edge etch chamber or module, a physical vapor deposition (PVD) chamber or module, a chemical vapor deposition (CVD) chamber or module, an atomic layer deposition (ALD) chamber or module, an atomic layer etch (ALE) chamber or module, an ion implantation chamber or module, a track chamber or module, and any other semiconductor processing systems that may be associated or used in the fabrication and/or manufacturing of semiconductor wafers.

As noted above, depending on the process step or steps to be performed by the tool, the controller might communicate with one or more of other tool circuits or modules, other tool components, cluster tools, other tool interfaces, adjacent tools, neighboring tools, tools located throughout a factory, a main computer, another controller, or tools used in material transport that bring containers of wafers to and from tool locations and/or load ports in a semiconductor manufacturing factory.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. As used herein, the phrase at least one of A, B, and C should be construed to mean a logical (A OR B OR C), using a non-exclusive logical OR, and should not be construed to mean "at least one of A, at least one of B, and at least one of C." It should be understood that one or more steps within a method may be executed in different order (or concurrently) without altering the principles of the present disclosure.

What is claimed is:

1. A method for diagnosing a particle removal system of a substrate processing system, comprising:
dispersing synthetic particles onto a substrate;
exciting the synthetic particles using a light source having a first predetermined wavelength;
measuring photoluminescence of the synthetic particles at a second predetermined wavelength that is different than the first predetermined wavelength and determining a first number of the synthetic particles on the substrate;
at least one of moving the substrate through a chamber or processing the substrate in the chamber of the substrate processing system;
exciting the synthetic particles using light having the first predetermined wavelength;
measuring photoluminescence of the synthetic particles at the second predetermined wavelength that is different than the first predetermined wavelength; and
determining a second number of the synthetic particles on the substrate based on the measuring.

2. The method of claim 1, wherein the synthetic particles have N different sizes, wherein N is an integer greater than one.

3. The method of claim 2, wherein the light source produces light at N first predetermined wavelengths and measurement is made at N second predetermined wavelengths.

4. The method of claim 3, wherein N first predetermined wavelengths are distinct, and wherein the N second predetermined wavelengths are distinct.

5. The method of claim 3, wherein excitation at the N first predetermined wavelengths and measurement at the N second predetermined wavelengths are performed sequentially, respectively.

6. The method of claim 3, wherein excitation at the N first predetermined wavelengths and measurement at the N second predetermined wavelengths are performed in an overlapping manner or a partially overlapping manner, respectively.

7. The method of claim 1, wherein the chamber is selected from a group consisting of a transport handling chamber, a buffer station, a metrology station and a processing chamber of the substrate processing system.

8. The method of claim 1, wherein the synthetic particles have a size between 5 nm and 30 nm.

9. The method of claim 1, further comprising diagnosing operation of a particle removal system associated with the chamber based on the first count and the second count.

10. The method of claim 1, further comprising altering operation of a particle removal system associated with the chamber based on the first count and the second count.

11. A method for diagnosing particle movement in a chamber of a substrate processing system, comprising:
dispersing synthetic particles into the chamber of the substrate processing system;
at least one of operating the chamber or moving the substrate through the chamber of the substrate processing system;
exciting the synthetic particles using light having a first predetermined wavelength;
measuring photoluminescence of the synthetic particles at a second predetermined wavelength that is different than the first predetermined wavelength; and
determining a number of the synthetic particles that moved from the chamber onto the substrate based on the measuring.

12. The method of claim 11, further comprising:
prior to the at least one of operating the chamber or moving the substrate through the chamber:
exciting the synthetic particles using light having a first predetermined wavelength; and
measuring photoluminescence of the synthetic particles at a second predetermined wavelength that is different than the first predetermined wavelength and determining a first number of the synthetic particles on the substrate.

13. The method of claim 11, wherein the synthetic particles have N different sizes, wherein N is an integer greater than one.

14. The method of claim 13, wherein the light source produces light at N first predetermined wavelengths and measurement is made at N second predetermined wavelengths.

15. The method of claim 14, wherein the N first predetermined wavelengths are distinct, and wherein the N second predetermined wavelengths are distinct.

16. The method of claim 14, wherein excitation at the N first predetermined wavelengths and measurement at the N second predetermined wavelengths are performed sequentially, respectively.

17. The method of claim 14, wherein excitation at the N first predetermined wavelengths and measurement at the N second predetermined wavelengths are performed in an overlapping manner or a partially overlapping manner, respectively.

18. The method of claim 11, wherein the chamber is selected from a group consisting of a transport handling chamber, a buffer station, a metrology station and a processing chamber of the substrate processing system.

19. The method of claim 11, wherein the synthetic particles have a size between 5 nm and 30 nm.

20. The method of claim 11, further comprising diagnosing operation of a particle removal system associated with the chamber based on the first count and the second count.

21. The method of claim 11, further comprising altering operation of a particle removal system associated with the chamber based on the first count and the second count.

22. A method for determining particle adders in a substrate processing system, comprising:
at least one of operating a chamber or moving the substrate through the chamber of the substrate processing system;
exciting particles on the substrate using light having N first predetermined wavelengths, where N is an integer greater than one;
measuring photoluminescence of the particles at N second predetermined wavelengths that are different than the N first predetermined wavelengths; and
determining a number of the particles on the substrate based on the measuring.

23. The method of claim 22, further comprising:
prior to moving the substrate through the chamber:
exciting particles on the substrate using light having the N first predetermined wavelengths; and
measuring photoluminescence of the synthetic particles at N second predetermined wavelengths that are different than the N first predetermined wavelengths and determining an initial number of the particles on the substrate.

24. The method of claim 22, wherein the particles have at least N different sizes.

25. The method of claim 22, wherein the N first predetermined wavelengths are distinct, and wherein the N second predetermined wavelengths are distinct.

26. The method of claim 22, wherein the excitation at the N first predetermined wavelengths and measurement at the N second predetermined wavelengths is performed sequentially, respectively.

27. The method of claim 22, wherein the excitation at the N first predetermined wavelengths and measurement at the N second predetermined wavelengths is performed in an overlapping manner or a partially overlapping manner, respectively.

28. The method of claim 22, wherein the chamber is selected from a group consisting of a transport handling chamber, a buffer station, a metrology station and a processing chamber of the substrate processing system.

29. The method of claim 22, wherein the particles have a size between 5 nm and 30 nm.

\* \* \* \* \*